United States Patent [19]

Lui et al.

[11] Patent Number: 5,463,150
[45] Date of Patent: Oct. 31, 1995

[54] PROCESS FOR PREPARING HEXAFLUOROBUTENE

[75] Inventors: Norbert Lui, Köln; Albrecht Marhold, Leverkusen; Dietmar Bielefeldt, Ratingen, all of Germany

[73] Assignee: Bayer Aktiengesellschaft, Leverkusen, Germany

[21] Appl. No.: 195,236

[22] Filed: Feb. 14, 1994

[30]   Foreign Application Priority Data

Feb. 19, 1993 [DE]   Germany .................. 43 05 163.4

[51] Int. Cl.⁶ .................................................. C07C 17/34
[52] U.S. Cl. ........................................ 570/157; 570/155
[58] Field of Search ............................ 570/228, 157, 570/155

[56]             References Cited

U.S. PATENT DOCUMENTS

T922,005   5/1974   Briggs ......................... 570/228
3,287,425   11/1966   Maynard .
3,739,036   6/1973   Valicenti et al. .
5,180,860   1/1993   Fernandez et al. .

FOREIGN PATENT DOCUMENTS 965069   7/1964   United Kingdom .

*Primary Examiner*—Alan Siegel
*Attorney, Agent, or Firm*—William C. Gerstenzang; Sprung Horn Kramer & Woods

[57]             ABSTRACT

1,1,1,4,4,4-Hexafluorobut-2-ene is prepared from chlorofluorobutanes of the formula (I)

$$CF_3\text{—}CH_2\text{—}CHCl\text{—}CX_3 \qquad (I)$$

in which the individual radicals X independently of each other represent chlorine and/or fluorine, by reaction with alkali metal fluoride in an aprotic polar solvent.

8 Claims, No Drawings

PROCESS FOR PREPARING HEXAFLUOROBUTENE

The present invention relates to a process for preparing 1,1,1,4,4,4-hexafluorobut-2-ene ($CF_3-CH=CH-CF_3$). 1,1,1,4,4,4-Hexafluorobut-2-ene can be converted by hydrogenation into 1,1,1,4,4,4-hexafluorobutane, in which there has been recent interest as foaming agent for the production of foam materials because it can substitute for the ecologically undesirable chlorofluorocarbons.

It is known that the action of potassium fluoride on hexachlorobutadiene in a carboxamide solvent gives 1,1,1,2,4,4,4-heptafluorobut-2-ene (see U.S. Pat. No. A 3 287 425). It was therefore to be expected that the action of potassium fluoride on 1,1,2,4,4-pentachlorobutadiene under the same conditions would allow 1,1,1,4,4,4-hexafluorobut-2-ene to be prepared. However, it has been found that 1,1,1,4,4,4-hexafluorobut-2-ene cannot be prepared in this way, since only resinous products are formed in this reaction (see Comparative Example 1).

It was also found that the action of potassium fluoride on 1,1,1-trifluoro-3,4,4-trichlorobut-3-ene under the above-mentioned conditions likewise gives only resinous products and not the 1,1,1,4,4,4-hexafluorobutane which would be expected in accordance with U.S. Pat. No. A 3 287 425 (see Comparative Example 2).

According to Applicants' earlier, as yet unpublished proposal, 1,1,2,4,4-pentachlorobutadiene is first reacted with hydrogen fluoride in the presence of catalysts to give 1,1,1,4,4,4-hexafluoro-2-chlorobutane and this is converted by elimination and hydrogenation into 1,1,1,4,4,4-hexafluorobutane.

A somewhat simplified picture is given by reaction equations as follows:

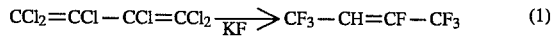  (1)

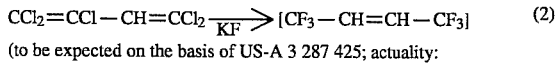  (2)

(to be expected on the basis of US-A 3 287 425; actuality: resin formation)

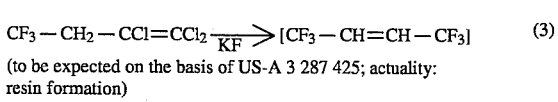  (3)

(to be expected on the basis of US-A 3 287 425; actuality: resin formation)

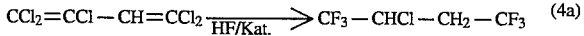  (4a)

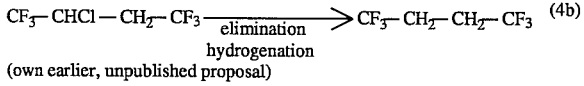  (4b)

(own earlier, unpublished proposal)

Being able to prepare 1,1,1,4,4,4-hexafluorobut-2-ene and hence 1,1,1,4,4,4-hexafluorobutane by reaction of a chlorine-containing $C_4$ compound with potassium fluoride therefore appears unlikely.

A process has now been found for preparing 1,1,1,4,4,4-hexafluorobut-2-ene, which is characterized in that chlorofluorobutanes of the formula (I)

$$CF_3-CH_2-CHCl-CX_3 \quad (I)$$

in which the individual radicals X independently of each other represent chlorine and/or fluorine, are reacted with alkali metal fluoride in an aprotic polar solvent.

The following reaction equation illustrates the process of the invention by way of example:

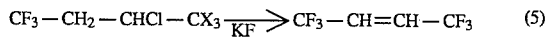  (5)

Suitable starting materials of the formula (I) for the process of the invention can be obtained, for example, by reacting 1,1,3,4,4-pentachlorobuta-1,3-diene with hydrogen fluoride in the presence of catalysts (for example Lewis acids). This generally gives mixtures of compounds of the formula (I) in the components of which the $CX_3$ group can be a $CCl_3$, $CCl_2F$, $CClF_2$ or a $CF_3$ group. It is a particular advantage of the process of the invention that such mixtures of compounds of the formula (I) can be used. Naturally it is also possible to use any of the individual compounds of the formula (I), for example 1,1,1-trifluoro-3,4,4,4-tetrachlorobutane,
1,1,1,4-tetrafluoro-3,4,4-trichlorobutane,
1,1,1,4,4-pentafluoro-3,4-dichlorobutane or
1,1,1,4,4,4-hexafluoro-3-chlorobutane.

Suitable alkali metal fluorides are in particular sodium and potassium fluoride and also mixtures of these with a small amount of caesium fluoride. Preferably potassium fluoride is used. The alkali metal fluoride is preferably used in dried form. The drying can be carried out, for example, by heating to from about 200° to 490° C. or by admixing with a high-boiling solvent, for example the solvent required for the reaction of the invention, and then distilling off a small amount of the solvent together with any water present.

The alkali metal fluoride can, for example, be used in the stoichiometrically required amount or in excess. When using one mole of pure 1,1,1,4,4,4-hexafluoro-3-chlorobutane, 1 mole of alkali metal fluoride is stoichiometrically required; when using a starting material with a lower degree of fluorination (in pure form or in admixture with 1,1,1,4,4,4-hexafluoro-3-chlorobutane), a further mole of alkali metal fluoride is stoichiometrically required for each mole of further chlorine present in the starting material, up to 5 mol of alkali metal fluoride when using pure 1,1,1-trifluoro-3,4,4,4-tetrachlorobutane.

Preferably the alkali metal fluoride is used in an amount which is between the stoichiometrically required amount and a 5-fold molar excess thereof.

Suitable aprotic polar solvents are, for example: carbonamides having from 1 to 4 carbon atoms, $N-C_1-C_4$-mono- and $N-C_1-C_4$-dialkyl derivatives thereof, $C_1-C_4$-alkyl sulphoxides, $C_1-C_4$-sulphones, cyclic alkylene sulphones having from 5 to 6 ring atoms, cyclic alkylene carbonates having from 5 to 6 ring atoms, and lactones and lactams each having from 5 to 7 ring atoms. Preference is given to tetramethylene sulphone, N-methylpyrrolidone (NMP) and dimethylacetamide.

The aprotic polar solvent can be used, for example, in amounts of from 25 to 250 ml, based on 100 g of reactants used (alkali metal fluoride and compounds of the formula (I)).

The process of the invention can be carried out, for example, at temperatures in the range from 120° to 280° C. Preference is given to reaction temperatures in the range from 180° to 230° C.

The process of the invention can be carried out at reduced, atmospheric or superatmospheric pressure, the pressure being so chosen that the reaction products remain in the liquid phase or distil out of the reaction mixture during the reaction. Preference is given to pressures between atmospheric pressure and 100 bar.

The process of the invention can optionally be carried out in the presence of phase transfer catalysts. Suitable examples of such are crown ethers and quaternary nitrogen or phosphorus compounds. Phase transfer catalysts can, for example, be used in amounts of from 0 to 10% by weight, based on the hexafluorobutene used.

During the reaction or after the end of the reaction, the 1,1,1,4,4,4-hexafluorobut-2-ene produced can be separated off from the reaction mixture by distillation or other means.

The hydrogenation of 1,1,1,4,4,4-hexafluorobut-2-ene to give 1,1,1,4,4,4-hexafluorobutane can, for example, be carried out catalytically in a manner which is conventional per se in the liquid or gaseous phase. Suitable catalysts are conventional hydrogenation catalysts, for example ones which contain palladium, nickel or compounds thereof.

In view of the prior art indicated in the introduction it is very surprising that 1,1,1,4,4,4-hexafluorobut-2-ene can be successfully prepared according to the invention in a simple manner and in good yields.

EXAMPLES

Comparative Example 1

226 g of 1,1,2,4,4-pentachlorobutadiene were added dropwise to 1200 ml of tetramethylene sulphone and 400 g of dried potassium fluoride at 190° C. over a period of 25 minutes. After 1 hour at 220° C. the reaction mixture became black and resinified. No 1,1,1,4,4,4-hexafluorobut-2-ene could be isolated.

Comparative Example 2

50 g of 1,1,1-trifluoro-3,4,4-tricylorobut-3-ene were added dropwise to 350 ml of tetramethylene sulphone and 80 g of dried potassium fluoride at 190° C. After 1.5 hours at from 200° to 220° C. the reaction mixture became black and resinified. No 1,1,1,4,4,4-hexafluorobut-2-ene could be isolated.

Example 1 According to the Invention 960 g of 1,2-dichloro-1,1,4,4,4-pentafluorobutane were added dropwise to a mixture of 3 l of distilled tetramethylene sulphone and 830 g of dried potassium fluoride at 190° C. and 1,1,1,4,4,4-hexafluorobut-2-ene was distilled off as it was formed. The product thus obtained was redistilled to give 650 g of 1,1,1,4,4,4-hexafluorobut-2-ene having a boiling point of 8° C at atmospheric pressure.

Example 2 According to the Invention 200 g of 2-chloro-1,1,1,4,4,4-hexafluorobutane were added dropwise to a mixture of 195 ml of distilled tetramethylene sulphone and 87 g of dried potassium fluoride at 190° C. and the 1,1,1,4,4,4-hexafluorobut-2-ene which formed was continuously distilled off. 135 g of 1,1,1,4,4,4-hexafluorobut-2-ene were obtained.

What is claimed is:

1. A process for preparing 1,1,1,4,4,4-hexafluorobut-2-ene, which comprises to react a chlorofluorobutane of the formula (I)

$$CF_3-CH_2CHCl-CX_3, \quad (I)$$

in which the —$CX_3$ group represents a member of the group consisting of $CCl_3$, $CCl_2F$ and $CClF_2$ with alkali metal fluoride in an aprotic polar solvent.

2. The process of claim 1, in which the alkali metal fluoride is used in an mount between the stoichiometrically required amount and a 5-fold molar excess thereof.

3. The process of claim 1, in which the aprotic polar solvent used is a carboxamide having from 1 to 4 carbon atoms, a N-$C_1$-$C_4$-mono- or a N-$C_1$-$C_4$-dialkyl derivative thereof, a $C_1$-$C_4$-alkyl sulphoxide, a $C_1$-$C_4$-sulphone, a cyclic alkylene sulphone having from 5 to 6 ring atoms, a cyclic alkylene carbonate having from 5 to 6 ring atoms, or a lactone or lactame each having from 5 to 7 ring atoms.

4. The process of claim 1, in which the aprotic polar solvent is used in an amount of from 25 to 250 ml, based on 100 g of reactants used.

5. The process of claim 1, which is carried out at a temperature in the range from 120° to 280° C.

6. The process of claim 1, which is carried out in the presence of a phase transfer catalyst.

7. The process of claim 1, in which during the reaction the 1,1,1,4,4,4-hexafluorobut-2-ene produced is separated off by distillation.

8. The process of claim 1, in which after the end of the reaction the 1,1,1,4,4,4-hexafluorobut-2-ene produced is separated off by distillation.

* * * * *